(12) United States Patent
Iversen (10) Patent No.: US 7,828,269 B2
(45) Date of Patent: Nov. 9, 2010

(54) DISPOSABLE VALVE UNIT FOR REGULATING A FLOW OF URINE

(75) Inventor: Jørgen Iversen, Store Heddinge (DK)

(73) Assignee: Unomedical A/S, Birkeroed (DK)

( * ) Notice: Subject to any disclaimer, the term of this patent is extended or adjusted under 35 U.S.C. 154(b) by 726 days.

(21) Appl. No.: 10/558,047

(22) PCT Filed: May 19, 2004
(Under 37 CFR 1.47)

(86) PCT No.: PCT/DK2004/000356
§ 371 (c)(1),
(2), (4) Date: Jun. 16, 2006

(87) PCT Pub. No.: WO2004/103229
PCT Pub. Date: Dec. 2, 2004

(65) Prior Publication Data
US 2007/0057222 A1    Mar. 15, 2007

(30) Foreign Application Priority Data
May 22, 2003    (DK) ................................ 2003 00771

(51) Int. Cl.
*F16K 3/26* (2006.01)
(52) U.S. Cl. .................. 251/319; 251/324; 604/323
(58) Field of Classification Search .................. 251/318, 251/319, 324; 604/322–326
See application file for complete search history.

(56) References Cited
U.S. PATENT DOCUMENTS 3,143,109 A * 8/1964 Gewertz ..................... 604/236
3,415,299 A * 12/1968 Hinman, Jr. et al. ......... 604/323
3,823,716 A * 7/1974 Hale ........................... 604/322
4,188,989 A    2/1980 Andersen (Continued)

FOREIGN PATENT DOCUMENTS

DK    158319 B    4/1990

(Continued)

OTHER PUBLICATIONS

International Search Report dated Sep. 6, 2004 for International Application No. PCT/DK2004/000356.

(Continued)

*Primary Examiner*—John Bastianelli
(74) *Attorney, Agent, or Firm*—Brinks Hofer Gilson & Lione (57) ABSTRACT

A valve unit for regulating a flow and a disposable urine bag are provided. The valve unit includes an inlet portion and an outlet portion separated from each other by a slide valve. The slide valve includes a female part in direct communication with the inlet portion and the outlet portion and a male part axially displaceable in liquid-proof contact with the female part. The male part includes a closing position wherein a portion of the male part is outside the female part and an open position wherein the male part allows liquid passage between the inlet portion and the outlet portion by means of a communication part. The female part includes a tubular member open at both ends and having a tubular wall extending along the entire length of the male part in the open position for deterring displacement of the male part to the closed position.

8 Claims, 7 Drawing Sheets

U.S. PATENT DOCUMENTS

| | | | |
|---|---|---|---|
| 4,306,705 A | 12/1981 | Svensson | |
| 4,423,741 A * | 1/1984 | Levy | 604/323 |
| 4,581,763 A * | 4/1986 | Olsen | 604/323 |
| 4,634,437 A | 1/1987 | Lowthian | |
| 4,844,415 A | 7/1989 | Nielsen et al. | |
| 5,087,251 A | 2/1992 | Heyman et al. | |
| 5,135,199 A * | 8/1992 | Cross et al. | 251/319 |

FOREIGN PATENT DOCUMENTS

| | | |
|---|---|---|
| GB | 1 310 581 | 3/1973 |
| GB | 2 390 547 A | 1/2004 |

OTHER PUBLICATIONS

International Preliminary Report on Patentability dated Aug. 23, 2005 for International Application No. PCT/DK2004/000356.

* cited by examiner

DISPOSABLE VALVE UNIT FOR REGULATING A FLOW OF URINE

This application is the National Stage of International Application No. PCT/DK2004/000356 filed May 19, 2004, which claims priority to Danish Application PA 2003 00771, filed May 22, 2003, these references are incorporated herein in their entirety.

FIELD OF THE INVENTION

The invention relates to a valve unit for regulating a flow of urine, said valve unit comprising an inlet portion and an outlet portion separated from each other by a slide valve, said slide valve comprising a female part in direct communication with the inlet portion and the outlet portion and a male part which is axially displaceable in parallel within the female part and in liquid-proof contact there with, said male part being configured for assuming two extreme positions, a closing position and an open position, in which closing position a part of the male part is situated outside the female part; and wherein the outer faces of the male part, being in the closing position and in the area where the inlet portion and the outlet portion connect to the female part, provide a liquid-proof blocking between inlet portion and outlet portion by means of a communication part.

The invention also relates to a disposable urine bag for collecting urine, said bag comprising an upper delimiting edge, a lower delimiting edge and side-delimiting edges, said edges delimiting a cavity in the bag, said upper delimiting edges being situated at the upper delimiting edge being in communication with means outside the bag, and said lower delimiting edge comprising a valve unit comprising an inlet part and an outlet part separated from each other by a slide valve, said slide valve comprising a female part in direct communication with the inlet portion and the outlet portion and a male part which is axially displaceable in parallel within the female part and in liquid-proof contact there with, said male part being configured for assuming two extreme positions, a closing position and an open position, in which closing position a part of the male part is situated outside the female part; and wherein the outer faces of the male part, being in the closing position and in the area where the inlet portion and the outlet portion connect to the female part, provide a liquid-proof blocking between inlet portion and outlet portion by means of a communication part; that the inlet portion communicates with the cavity of the bag; and the outlet portion is situated outside the delimiting edges of the bag.

Finally, the invention relates to use of the valve unit.

BACKGROUND

Regulation of urine flow is relevant in connection with use of urine bags, wherein a collection of urine takes place within the bag as such, and wherein the latter is subsequently to be emptied. Likewise, it may be relevant to regulate the urine flow in connection with the use of a catheter; and wherein the valve unit may optionally be mounted on the outlet end of the catheter thereby enabling regulated emptying.

In connection with the use of urine bags, such bag comprises an upper part, typically equipped with a non-return valve, to which a tubular member is connected which is in turn connected primarily to a catheter. The collection of urine takes place through the catheter tube, and wherein the non-return valve ensures that outflow does not take place through tube and catheter when the bag is filled and turned upside down. In connection with the manufacture of disposable urine bags, such bag will typically be completely-closed on the remaining sides, and therefore the only communication with the exterior takes place through said tube.

When the bag is filled, a corner will typically be torn off, the bag will be turned, following which it is emptied, and the disposable bag can be discarded. However, there is a high risk of the user's fingers being soiled with urine in this process, and therefore there is a risk of cross-contamination in connection with further treatment and, likewise, such urine-soiling is unhygienic.

An example of a disposable bag is known eg from U.S. Pat. No. 5,087,251, comprising an inlet opening for receiving urine, and wherein—opposite that opening—a valve is mounted for sluicing out liquid. However, this valve is an opening/closing valve requiring, as it is, quite some finger strength and, likewise, it is quite complex to manufacture and constitutes a considerably price-raising element in those cases where the bag is used as a disposable bag.

Likewise, slide valve units are known that consist of a female part and a male part displaceable therein and wherein liquid passage is enabled when the male part is in its open position such that the urine can be discharged, and wherein the valve ensures that the urine remains in the bag or in the catheter when the male part is in the closed position. The valve is used for the collecting bag, and therefore the valve can be opened and closed as needed.

BRIEF SUMMARY OF THE INVENTION

It is thus the object of the present invention to provide a valve unit and a disposable urine bag that are not associated with the drawbacks of the prior art systems and wherein it is possible in a simple manner to rupture the seal of the valve unit without having to apply considerable finger strength and without an ensuring risk of the user being soiled with urine, while simultaneously the valve, being a disposable valve, being so similar to the multiple-use valve that it is possible to use existing tools that undergo a slight adjustment for the manufacture of such. The construction also ensures that the disposable valve cannot be re-used.

This object is accomplished by means of a valve unit of the kind described above and wherein the male part is also in its open position completely enclosed by the female portion with respect to that part of the male part—the second part—which is, during the opening function, moved away from the inlet and outlet portions, for providing a disposable valve unit.

The object is also achieved by a disposable urine bag of the kind described above and wherein the male part is also in its open position completely enclosed by the female portion with respect to that part of the male part which is, during the opening function, moved away from the inlet and outlet portions—the second part—, for providing a disposable valve unit.

When replete with urine and to be discarded, the bag will be disconnected from its connection to the catheter. Subsequently it will be turned upside down, and the user will seize the valve unit.

When in its closing function no liquid is drawn out until the male part is displaced to occupy its opening function.

The male part having in its closing function an element which is outside the enclosing female function, it is possible to activate it by applying a pressure and a push to the element. As soon as the male element is pushed into the female part, it is impossible to move the male part unless tools or the like are used to push the male part back again, the male part now being completely enclosed by the female part inasmuch as the part of the male portion is concerned that is, by the opening function, moved away from the inlet and outlet parts, whereby no activation elements are present within the female part that enable a change in the position of the male part.

Thereby a disposable valve is accomplished, where it is ensured that the bag is not reused and without a risk of the user being soiled with urine and without a risk of contamination. In this context it is to be mentioned that the closing position distinguishes itself in it not being possible for the liquid to penetrate through the communication part, while it is ensured that, in the opening position, the liquid is able to travel through the communication part.

The communication part may have various physical configurations, as—in the case where the male part is shaped as a cylindrical unit—it will typically be a cylindrically transversal opening through the male portion and, in other cases, it can be configured in such a way that the male portion comprises two cylindrical elements, a first and a second part, that are connected to each other by at least one rib, of which, however, there may very well be several and such that a communication area is produced in this area that allows the liquid to travel through.

In one aspect of the present invention, it is accomplished that the part of the male part designated the first part which is moved towards the inlet and outlet parts during the opening function is also enclosed by the female part, whereby it is ensured to a higher degree that the valve unit cannot be reused.

In another aspect of the present invention, the communication part may be provided by an opening transversally through the male part and perpendicular to its longitudinal axis.

In another aspect of the present invention, the communication part may be provided by a male part that is divided into two parts and further including at least one rib that connects the two parts of the male part together.

In another aspect of the present invention, both the inlet part and the outlet part comprise a tubular member.

In another aspect of the present invention, the female part includes a closure plate for providing a closed bottom so that it is impossible even by use of tools, such as a slim cylindrical object to push the male part situated within the female part, the closure plate ensuring that when in its open position, it is impossible to push the male part back due to the arrangement of the closure plate.

The invention will now be explained in further detail with reference to the drawing, in which.

BRIEF DESCRIPTION OF THE DRAWINGS

DETAILED DESCRIPTION OF THE INVENTION

Figure 1:
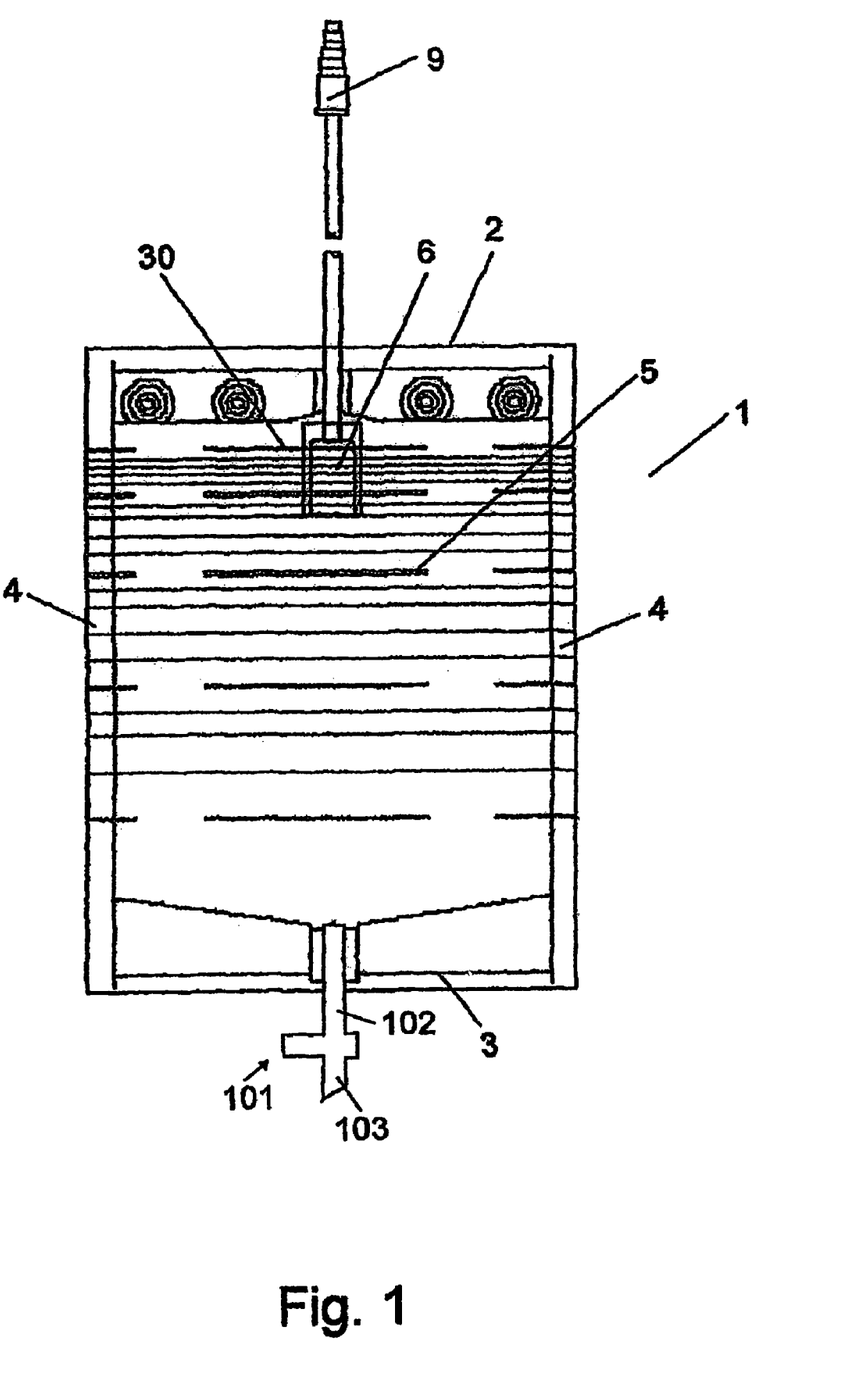
FIG. 1 shows a disposable urine bag comprising a non-return valve connected to a tubular element and, opposite this, a valve unit mounted in the bag.

FIG. 1 shows a disposable urine bag (1) manufactured from two essentially transparent plastics sheets being at their periphery sealed and connected to each other, preferably by a welding, and for providing a cavity (5) in which the urine may collect. Thus, the seals comprise an upper delimiting edge (2), a lower delimiting edge (3) and side-delimiting edges (4) that constitute an unbroken line; however, such that it is possible to travel past at the top and at the bottom as will be described below. The bag may also have other shapes: it may be round, elliptic, etc.

In the upper delimiting area (30) and inside the bag there is provided a non-return valve (6) ensuring that liquid may flow into the bag when the bag is suspended in level and with its valve unit (101) facing downwards, and where the non-return valve will prevent outflow of liquid there through when the bag is turned upside down to the effect that the valve unit (101) is caused to face upwards. The non-return valve (6) is connected to a plastics tube also designated means (9) located outside the bag. This plastics tube is typically connected to a catheter for collecting urine. Opposite the upper delimiting area (30), a valve unit (101) is arranged at the other end, comprising an inlet part (102) in the form of a tubular member of plastics situated within the bag as such and providing passage through the lower delimiting edge, whereby it is connected in a liquid-proof relationship to the delimiting edge; and wherein it communicates with the cavity (5).

Figure 2A:
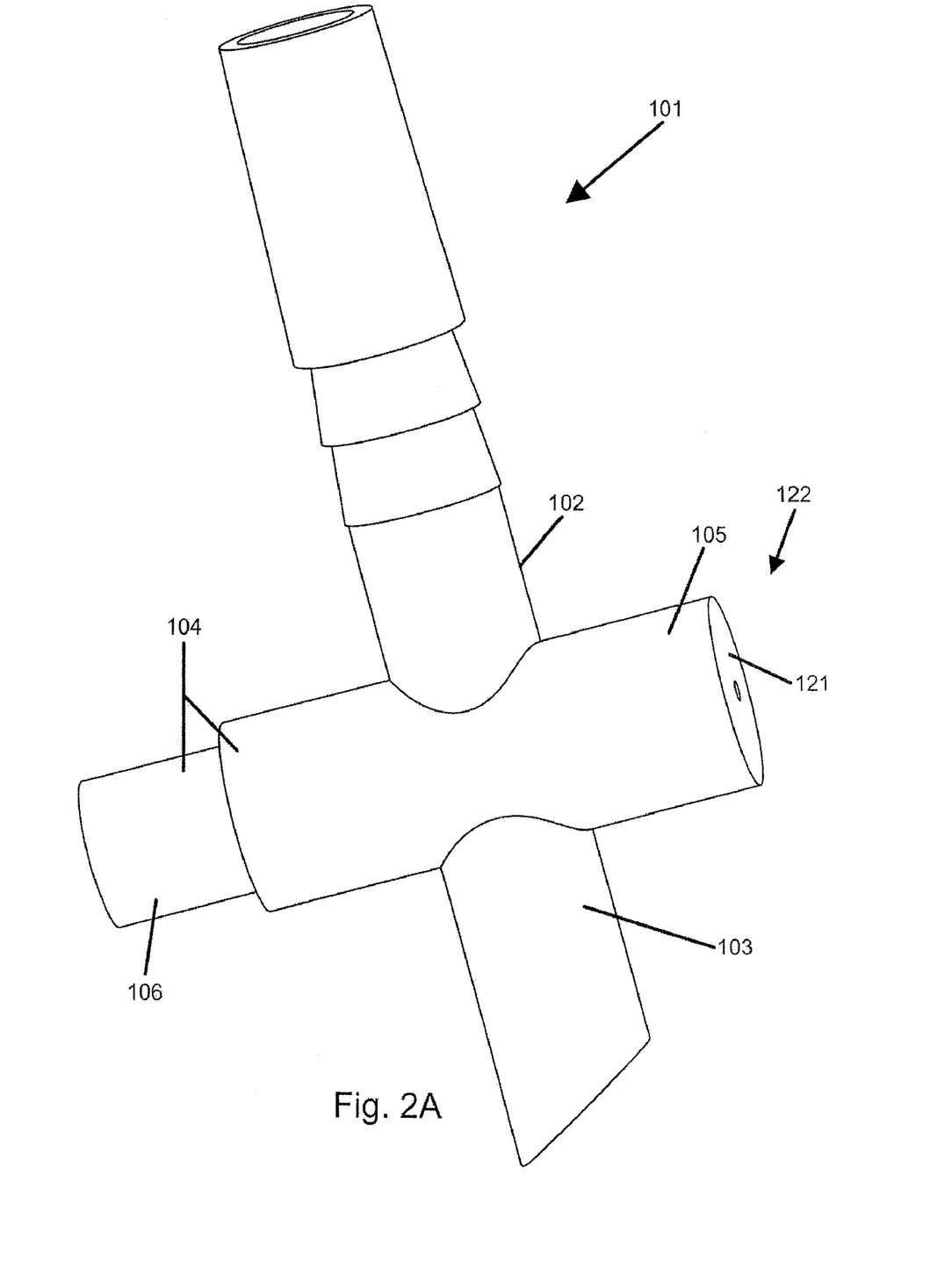
FIG. 2A shows a first exemplary embodiment of the valve unit according to the invention.

Firstly, FIG. 2A shows the valve unit (101) in a first exemplary embodiment comprising an essentially circular female part (105) being, at the one end, closed by a closure plate (121), while, at the other cylindrical end, it is open for receiving a male part (106), and wherein the outer shape of the male part is congruent with the inner faces of the female part, thereby establishing a sliding fit between the two parts and such that they are in liquid-proof abutment on each other. The male part slides within the female part for providing a slide valve (104) that is able to regulate a flow of liquid and in this case urine. The liquid enters an inlet part (102) and travels through the valve in the communication part when in its open position and out through the outlet part (103). Both inlet part and outlet part are essentially circular tubular members manufactured from a plastics material and injection moulded integrally with the female part (105) as such, by which a kind of intersection is provided, inlet part and outlet part being axially parallel and axially coincident and with this axis perpendicular to the longitudinal axis of the female part (105). Typically the outlet part (103) will be cut off diagonally thereby reducing the risk of dripping when the liquid is discharged.

Figure 2B:
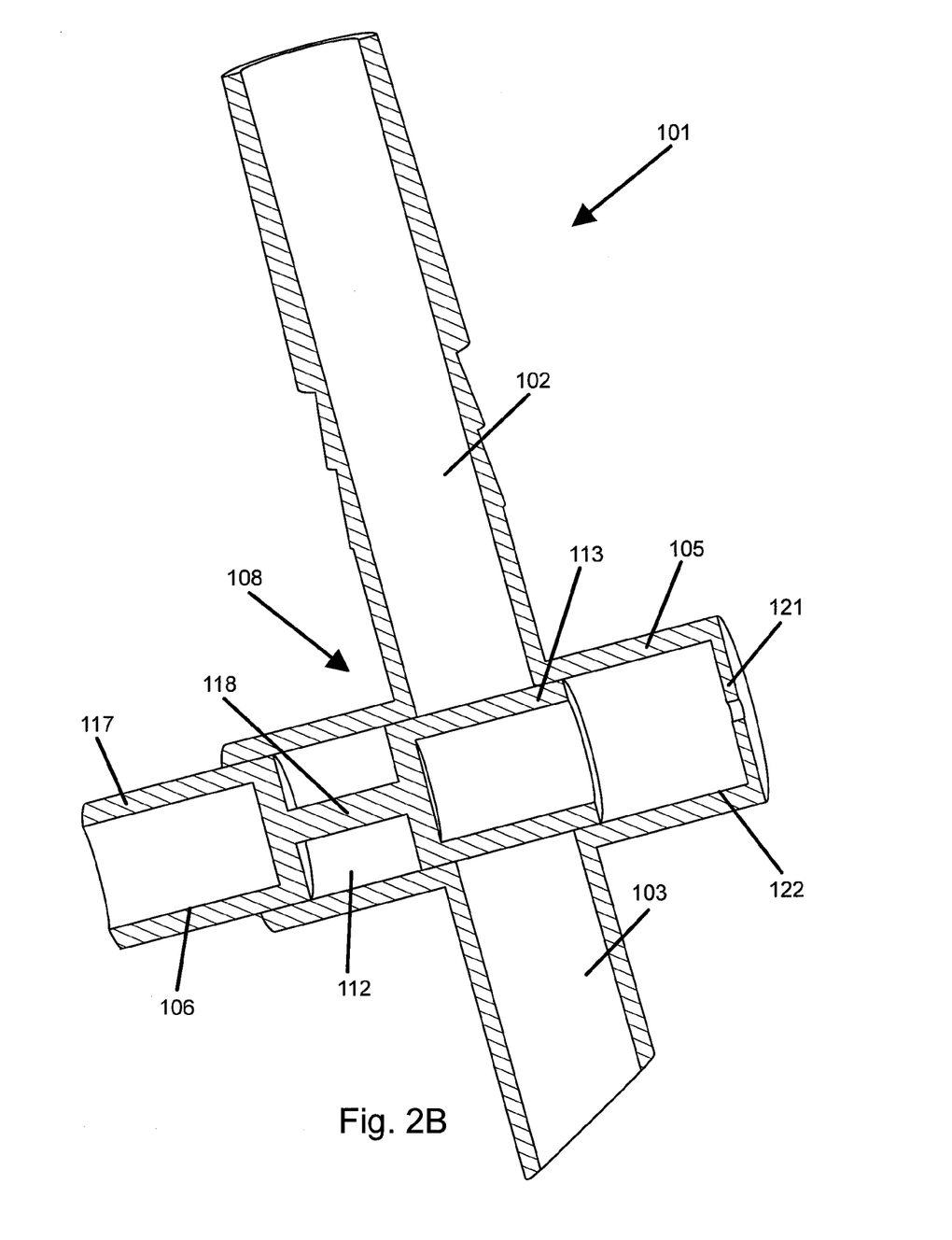
FIG. 2B is a sectional view along the central plane of the valve unit shown in FIG. 2 and wherein the male part is in its closing function.

FIG. 2B is a sectional view along the median plane of the valve unit shown in FIG. 2A, comprising the inlet part (102) and the outlet part (103); and wherein the valve is in its closing position (108). In this case, the male part (106) comprises two cylindrical parts: a first part (117) and a second part (113) on the faces that face towards each other and are connected to each other by means of a rib (119), of which there is at least one; however, there may be several. In both cases the rib is arranged perpendicular to the closed end faces of the two parts (113 and 117) and corresponding to the centre. In the closing position, the second part (113) will be situated such that it is arranged between the inlet part (102) and the outlet part (103), such that liquid cannot travel between the two parts. The first part (117) as such is arranged outside the female part such that it is possible to move the male part inside the female part by pressing and pushing that part, whereby the second part (113) moves away from the inlet part (102) and the outlet part (103) and thus no longer acts as a blocking. FIG. 2B shows a first position corresponding to the closure position and when the male part is pushed entirely away to the opening position, the depiction shown in FIG. 2C results.

Figure 2C:
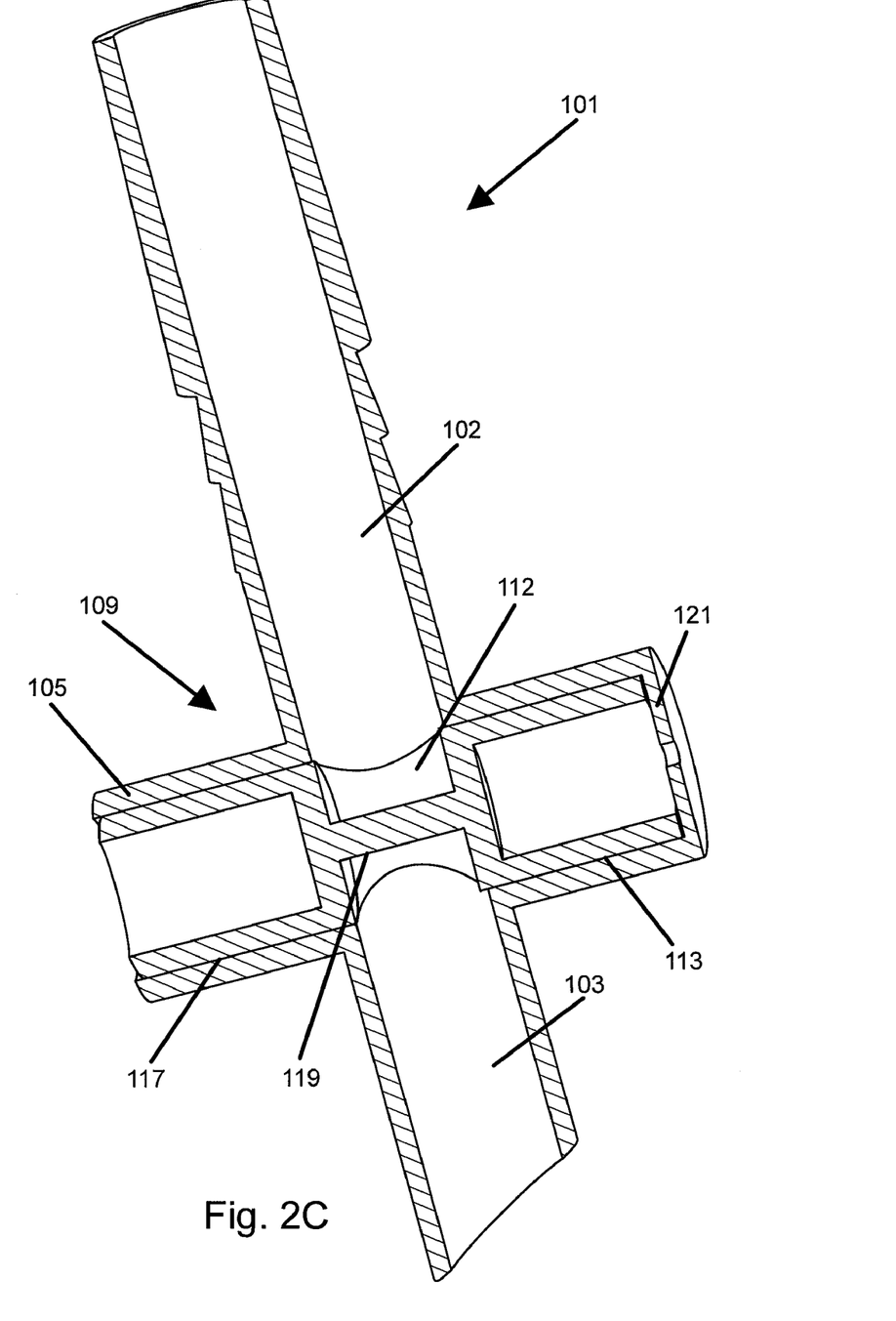
FIG. 2C is a sectional view along the central plane of the valve unit shown in FIG. 2, and wherein the male part is in its opening function.

It shows that the second part (113) is now moved away from the inlet and outlet parts to the effect that the communication part (112) is constituted by the area in which the rib (119) is situated. In other words, the liquid is now able to pass from the inlet portion (102) and through the outlet part (103), the only kind of blocking now being the rib (119) which, in itself, serves only to modify the flow conditions in the outflowing liquid, but does not prevent its flow. Here the communication part (112) consists of a circular communication cylinder axially parallel and coincident with the first and the second part and hereby having an interruption corresponding to the rib. The second part (113) being completely down and with its end delimitation opposite the end where the rib is situated in close abutment on the closure plate (121), it is not possible to push it and thus perform a closure of the valve unit (101). Likewise, the first part (117) is configured such that this part is also enclosed by the female part (105) and therefore the entire male part is completely enclosed by the female part.

Figure 3A:
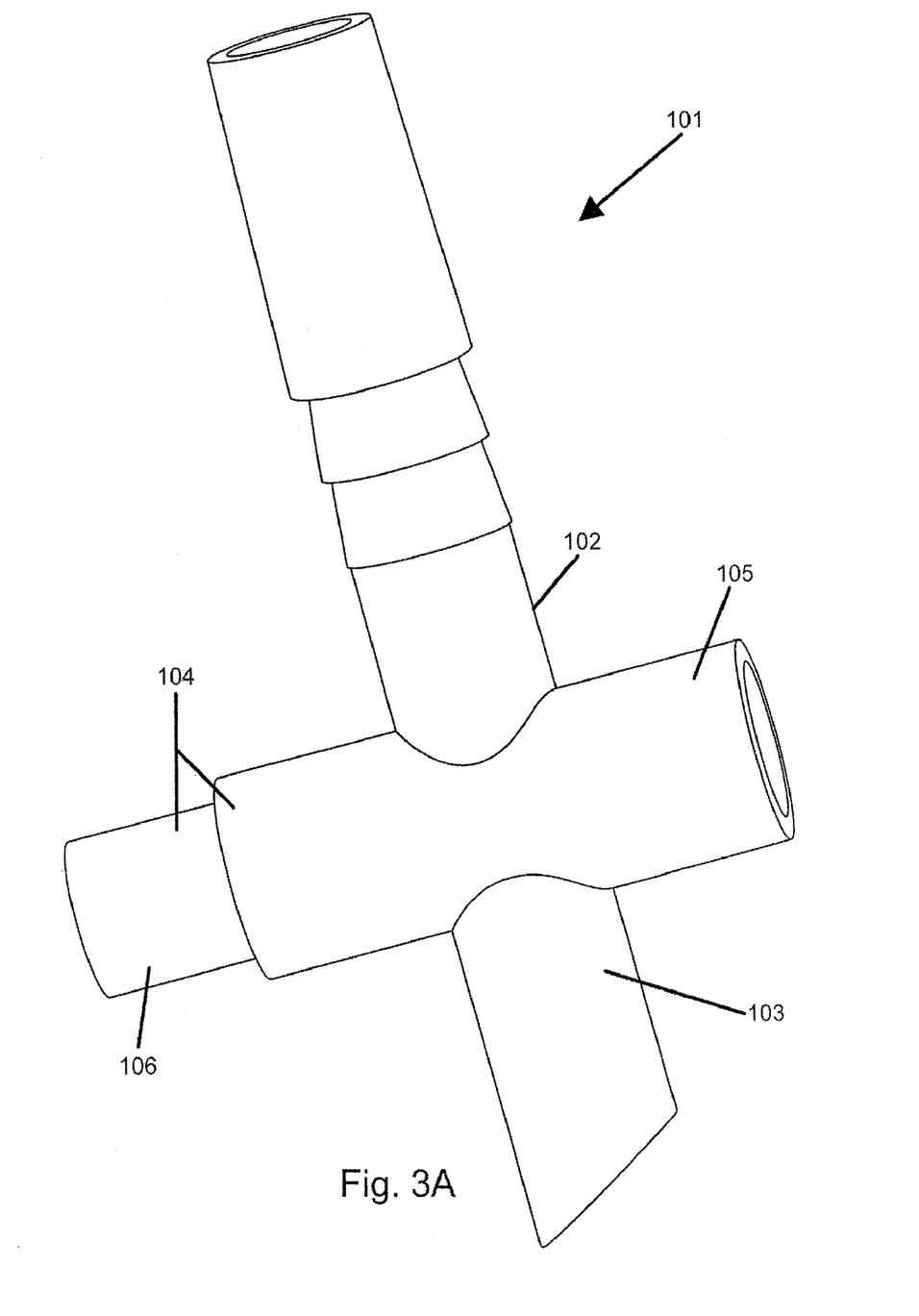
FIG. 3A shows an alternative embodiment of the valve unit according to the invention.
Figure 3B:
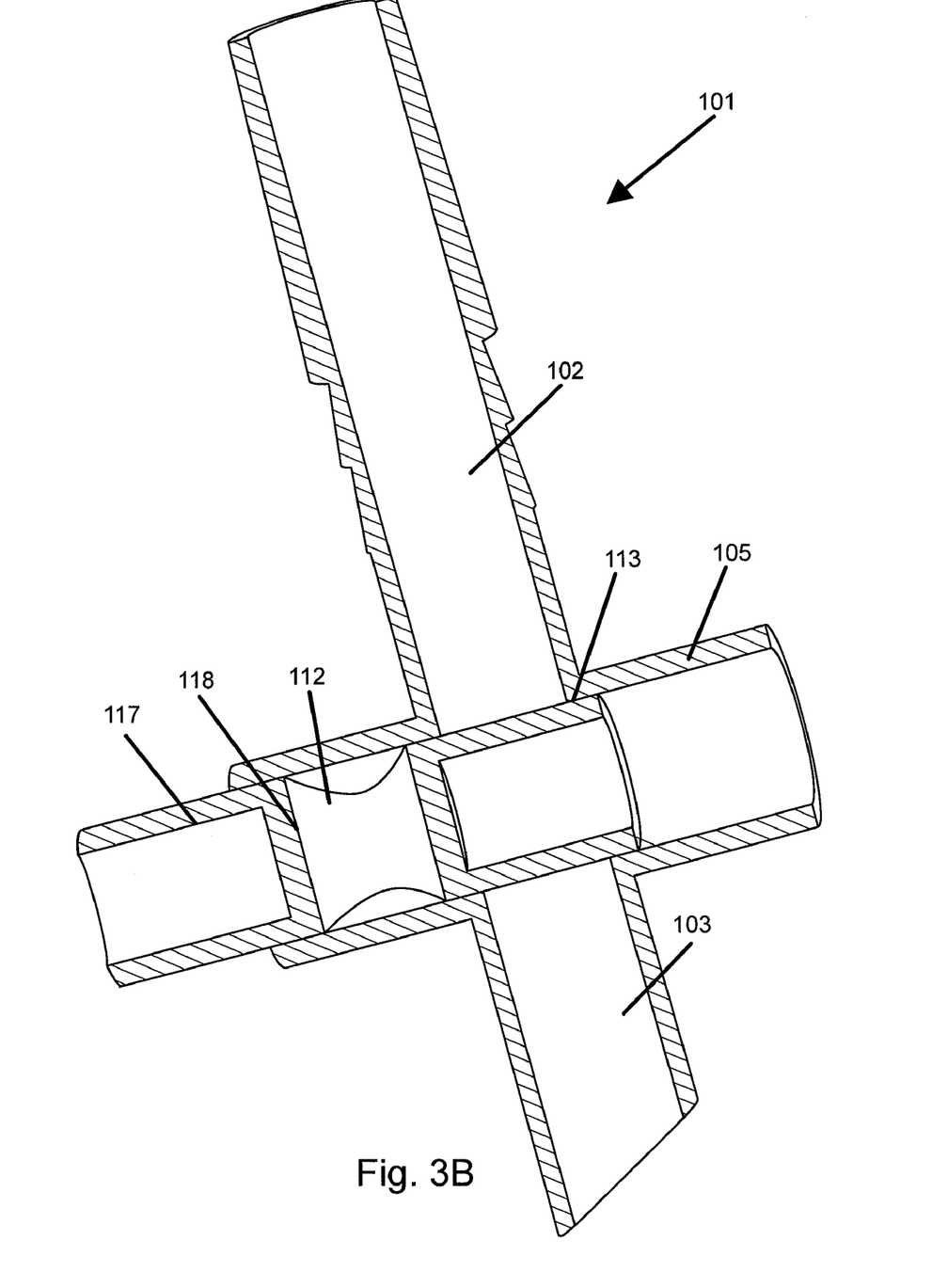
FIG. 3B is a sectional view along the central plane of the valve unit shown in FIG. 3A and wherein the male part is in its closing position.
Figure 3C:
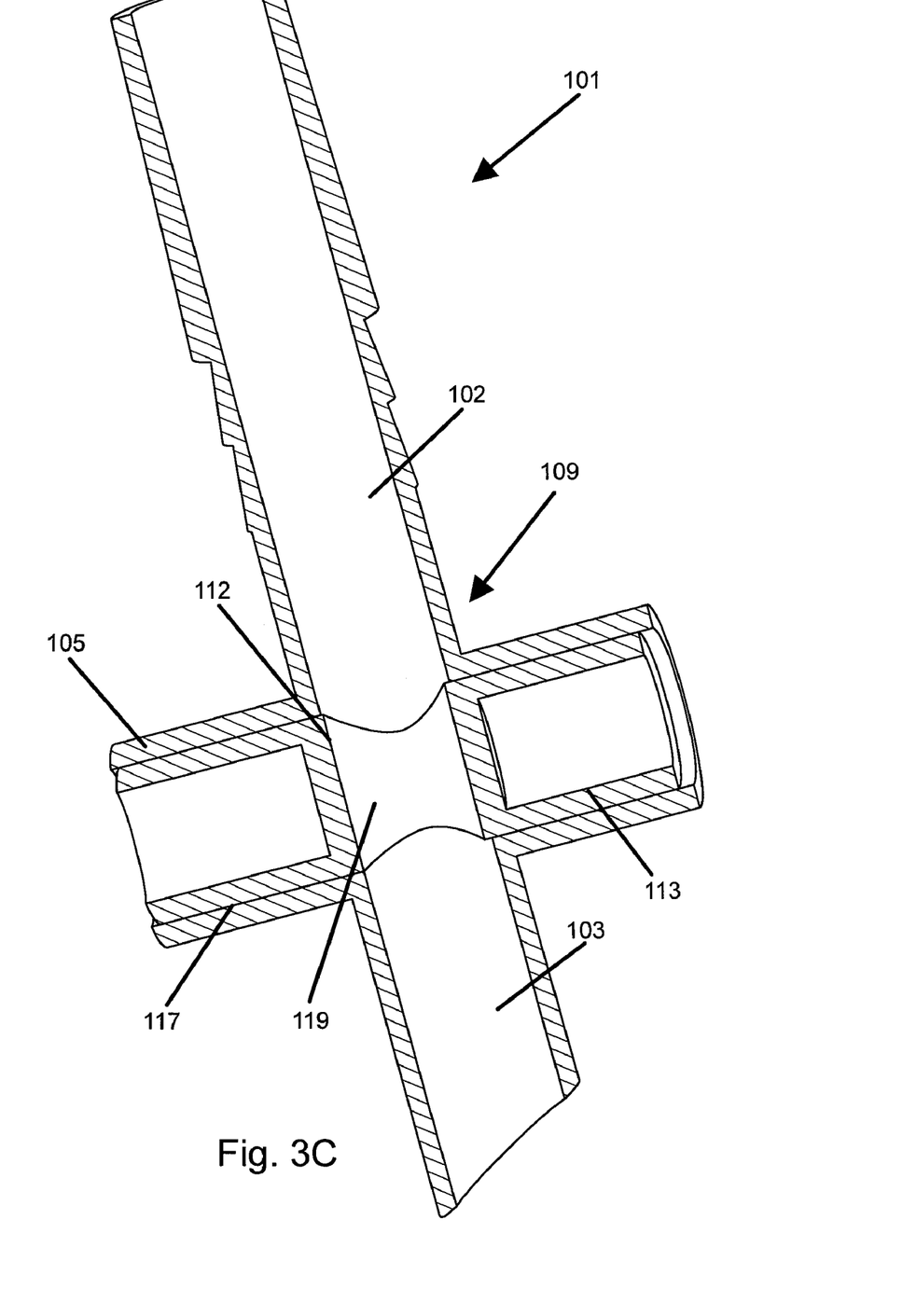
FIG. 3C is a sectional view along the central plane of the valve unit shown in FIG. 3A and wherein the male part is in its opening position.

FIG. 3A shows a valve unit (101) being essentially identical with the one shown in FIGS. 2A-C, wherein however the female part (105) does not, in this case, comprise a closure plate (121), but wherein the female part is a tubular element which is open at both ends and wherein, like the male part shown in FIGS. 2A-C, it can slide there within and wherein FIGS. 3B-C show the male part in closed and open position, respectively.

FIGS. 3B-C show how, in this case, the male part has another shape, the male part also comprising, in this case, a first part (117) and a second part (113) having a communication area (118) configured at a communication part (112) produced in that the male part (106) is as a whole formed as an essentially cylindrical unit, but wherein, corresponding to its central portion a bore is produced perpendicular to the longitudinal axis of the male part for providing a cylindrical opening transversally through the male part. As mentioned, this brings about the communication part (112).

FIG. 3C shows the case in which the second part (113) is moved away from the area between inlet part (102) and outlet part (103) for producing the opening function, and wherein the longitudinal axis of the communication part (112) is axially parallel and coincident with the axes of the inlet part (102) and the outlet part (103), respectively. Thus, there is unimpeded passage for liquid through inlet portion, outlet portion and communication part. In the opening position the male part is completely enclosed by the female part, inasmuch as the portion of the male part is concerned which has a smaller outer circumference than the inner circumference of the female part. Besides, the male part is configured cylindrically with regard to the part which is, in both its open and its closed position, enclosed by a cylindrical part of the female part and is not a constituent of the communication part. In that case the female part (105) is, as mentioned, open at both ends. It should be mentioned that, inasmuch as the first and second embodiments, shown in FIG. 2A-C and FIG. 3A-C, respectively, are concerned, it is an option for the female part (105) to comprise the closure plate (121) for providing a closed bottom (122), and likewise it is possible for the female part to be open at both ends.

The shown embodiments demonstrate the principle of the invention that may, however, comprise a number of other embodiments, for instance that the male and female portions may be square, triangular. The communication part could be configured in other ways; either with a number of different ribs and optionally with a number of cylindrical bores perpendicular to the longitudinal axis of the male part, and likewise such communication areas could be of both circular, triangular, square cross-sections, depending on the relevant situation.

The valve unit is manufactured by injection moulding and in a suitable plastics material, eg PVC, PP, ABS.

The invention claimed is:

1. A valve unit for regulating a flow of urine, said valve unit comprising an inlet portion and an outlet portion separated from each other by a slide valve, said slide valve comprising a valve housing formed as a female part in direct communication with the inlet portion and the outlet portion, and a valve body formed as a male part being axially displaceable in parallel and in liquid-proof contact with the female part, said male part being configured for assuming two positions, a closing position and an open position, in which closing position a portion of the male part is outside the female part; that, in the closing position and in the area where the inlet portion and the outlet portion connect to the female part, outer faces of the male part provide a liquid-proof blocking between the inlet portion and the outlet portion; that, in the open position, the male part allows liquid passage between said inlet portion and said outlet portion by means of a communication part; wherein said female part comprises a tubular member open at both ends and having a tubular wall extending along the entire length of said male part in said open position to completely enclose said valve body in said open position with no portion of said valve body projecting from said valve housing, for deterring displacement of said valve body to said closed position.

2. A valve unit according to claim 1, said closing position and open position being two extreme positions of said male part.

3. A valve unit according to claim 1, wherein the communication part is provided by an opening transversally through the male part and perpendicular to its longitudinal axis.

4. A valve unit according to claim 1, wherein the communication part comprises at least one rib that connects a first part and a second part of the male part.

5. A valve unit according to claim 1, wherein both the inlet portion and the outlet portion comprise a tubular member.

6. A disposable urine bag for collecting urine, said bag comprising an upper delimiting edge, a lower delimiting edge, and side-delimiting edges, said edges defining a cavity in the bag, said upper delimiting area situated at the upper delimiting edge being in communication with means outside the bag, and said lower delimiting edge comprising a valve unit comprising an inlet portion and an outlet portion separated from each other by a slide valve, said slide valve comprising a valve housing formed as a female part in direct communication with the inlet portion and the outlet portion, and a valve body formed as a male part being axially displaceable in parallel and in liquid-proof contact with the female part, said male part configurable into a closing position wherein a portion of the male part is outside the female part; so that outer faces of the male part provide a liquid-proof blocking between the inlet portion and the outlet portion; and an open position, wherein the male part allows liquid passage between inlet portion and outlet portion by means of a communication part; that the inlet portion communicates with the cavity of the bag; and the outlet portion is situated outside the delimiting edges of the bag, wherein said female part comprises a tubular member open at both ends and having a tubular wall extending along the entire length of said male part in said open position to completely enclose said valve body in said open position with no portion of said valve body projecting from said valve housing, for deterring displacement of said valve body to said closed position.

7. The disposable urine bag of claim 6, wherein the closing position and the open position comprise two extreme positions of the male part.

8. A valve unit for regulating a flow of urine, said valve unit comprising:
- an inlet portion and an outlet portion separated from each other by a slide valve, said slide valve comprising:
    - a valve housing formed as a female part in direct communication with the inlet portion and the outlet portion, and
    - a valve body formed as a male part being axially displaceable in parallel and in liquid-proof contact with the female part, said male part configurable into a closing position wherein a portion of the male part is outside the female part at a first end of said female part so that outer faces of the male part provide a liquid-proof blocking between the inlet portion and the outlet portion; and an open position wherein the male part allows liquid passage between the inlet portion and the outlet portion by means of a communication part;
- wherein said female part comprises a tubular member closed by a rigid closure plate at a second end opposite said first end and having a tubular wall extending along the entire length of said male part in said open position to completely enclose said valve body in said open position with no portion of said valve body projecting from said valve housing, for deterring displacement of said valve body to said closed position.

* * * * *